United States Patent [19]

Imer

[11] Patent Number: 5,633,005

[45] Date of Patent: May 27, 1997

[54] DIMETICON PASTILLES

[75] Inventor: Faruk Imer, Cologne, Germany

[73] Assignee: Bolder Arzneimittel GmbH, Cologne, Germany

[21] Appl. No.: 570,206

[22] Filed: Dec. 11, 1995

Related U.S. Application Data

[63] Continuation of Ser. No. 244,625, filed as PCT/EP92/02014, Sep. 2, 1992, abandoned.

[30] Foreign Application Priority Data

Dec. 5, 1991 [DE] Germany ................ 41 40 116.6

[51] Int. Cl.$^6$ ................................... A61K 9/68
[52] U.S. Cl. .................. 424/440; 424/464; 424/474
[58] Field of Search ........................ 424/440, 474, 424/464

[56] References Cited

U.S. PATENT DOCUMENTS

| | | | |
|---|---|---|---|
| 2,951,011 | 8/1960 | Feinstone | 167/55 |
| 3,382,150 | 5/1968 | Grass et al. | 167/82 |
| 4,396,604 | 8/1983 | Mitra | 424/154 |
| 5,073,384 | 12/1991 | Valentine | 424/474 |

FOREIGN PATENT DOCUMENTS

| | | |
|---|---|---|
| 0 425 450 A2 | 5/1991 | European Pat. Off. . |
| 1-60 235/09 | 10/1989 | Hungary . |
| A 2 033 915 | 5/1980 | United Kingdom . |
| 2 195 891 | 10/1987 | United Kingdom . |

OTHER PUBLICATIONS

Walter Rahn, "Pharmazeutische Zeitung" pp. 2214–2218, Oct. 14, 1982.

*Primary Examiner*—D. Gabrielle Phelan
*Attorney, Agent, or Firm*—Banner & Witcoff, Ltd.

[57] ABSTRACT

The invention concerns pastilles made from completely or partly water-soluble, natural and/or synthetic polymers selected from the group comprising gums, alginates, carrageen, starch, pectin and gelatin and containing polydimethylsiloxanes (dimeticon, simethicone). The invention also concerns a method of producing such pastilles.

11 Claims, No Drawings

DIMETICON PASTILLES

This application is a continuation of application Ser. No. 08/244,625, filed as PCT/EP92/02014 Sep. 2, 1992, now abandoned.

The invention relates to pastilles on the basis of certain natural or synthetic polymers comprising poly (dimethylsiloxanes) as an active substance which is commercially available by the international non-proprietary name Dimeticon or Simethicone.

By the term pastilles there are generally understood—see also W. Rahn, Pharmazeutische Zeitung, pg. 2214–2218 (1982)—preparations which can be sucked or chewed in the mouth. Essentially, there is differentiated between tablets, hard candies and gum-pastilles (also designated as gum-candies).

The processes for producing these offering forms are basically distinguished from another.

Tablets are pressed on tablet compressing machines. To this end, the tablet mass is to be prepared by mixing and granulating. Several authors have already worked with granulating methods of Dimeticon which is difficult to process.

Candies are prepared by mixing saccharose and glucose-syrup, cooking the resulting mixture at about 130° C., removing most of the water in vacuo to a residual water content of from 0.5 to 2% water from the mass. Active substances and flavors are added to the highly viscous candy mass, cooled down to about 85° C., and admixed by kneading. The candy mass while continuously cooled is drawn into strands, shaped and cut in tapered rollers and other candy machines. Due to the viscosity of the candy mass, the distribution of the active substance is known to be rather non-uniform.

Gum pastilles are prepared by first dissolving hydrocolloids, for example gum arabic, together with saccharose, glucosesyrup, sorbitol, xylitol and others, in water in an agitator vessel, and emulsifying or suspending, espectively, the active substances in this base mass. The thus obtained casting composition is cast into so called powder trays. These are for example flat wooden boxes having a size of 80 cm×40 cm, which have been filled with starch, especially corn starch. By using a stamp board, the desired shapes are pressed into the smoothed powder and the warm casting composition will be, exactly metered, pumped into the thus obtained wells, whereby the cast mass is not bound to the powder. Tray by tray, 500 to 1000 pastilles, respectively, are thereby cast, stacked, and water is removed from the pastilles in drying chambers to about 10% of residual moisture within 3 to 4 days. The pastilles produced thereby are "depowdered" and then transferred to a final treatment.

Dimeticon is a water insoluble polysiloxane having a molecular weight of from about 1000 to 3000 which has been marketed since a long time as antiflatulence agent in different forms of administration by many offerers. For example, tablets, capsules, chewing tablets, and drops are commercially available. Due to the high viscous, oily consistency of Dimeticon, the substance can not be pressed into tablet form directly, without adjuvants and carrier means. Therefore, in prior art Dimeticon is frequently mixed with highly disperse carriers such as silica or alumina, optionally by using tabletting adjuvants or tabletting auxiliaries, that are incorporated into tablets. Also highly disperse silica is used frequently for the preparation of drops.

Upon oral application of tablets, capsules or drops the active substance Dimeticon will be released in the gastrointestinal tract, and will display its action by reducing the surface tension. Due to the high viscosity, oily consistency, and the highly hydrophobic properties of Dimeticon, it is often difficult to achieve a fine dispersion of the active substance, so that particularly with chewing tablets granules are formed to a larger or less extent. It is a disadvantage by administering drops that the whole active substance will be delivered in a relatively short period of time, and is disposable only in a non-divided form.

From Derwent Abstracts 91-60 235 (HU-00 5450) there are known preparations to be orally administered for the treatment of flatulence, said preparations containing Dimeticon and carriers on the basis of water-soluble carrier materials, melting without decomposition in the range of from 40° C. to 120° C. From 10 to 25% by weight of a preferably molten mixture is added to the molten carrier. The mixture contains natural and synthetic bodies, cross-linking and thickening agents, particularly polyvinyl chloride, polyvinyl acetate, dextran, micro-crystalline cellulose, polyacrylic acid, polyvinylpyrrolidone and/or inorganic stabilizers. An administration form is not mentioned. There is described, however, a special coating procedure for producing Dimeticon-tablets.

From EP-A-0 425 450 there are known anti-flatulence agents that consist of a free-flowing granulated mixture of from 50 to 90% by weight of a water soluble, agglomerated maltodextrine and from 10 to 50% by weight of a liquid, non-aqueous silicone oil, for example, Dimeticon. The composition is mixed with further adjuvants and is processed in a single dosage form to tablets, filled capsules or granules.

From U.S. Pat. No. 4,396,604 there are known pastilles which contain Dimeticon besides an antacidum. The hard candies described herein are prepared by adding an antacidum to a solution or suspension of sugar or sugar substitutes at high temperature, and then evaporating the water to a large extent in vacuo. After cooling the mixture, for example, to 85° C., Dimeticon is added by kneading. The candy mass is drawn to strands, cut and formed, respectively, in candy-machines. This results in relatively heavy candies having a weight from 3 to 6 g, but with an inaccurate distribution of the active substance.

It was therefore the object of the present invention to provide a new form of administration of Dimeticon by applying a casting process known per se from the preparation of confectionery, characterized by:

finest distribution of the active substance in the pastille, very accurate single dosing of the active substance, easy handling of the active substance which is otherwise difficult to handle, comfortable administration of the drug, and optimal distribution of the active substance in the stomach by slowly sucking the pastille.

The aforementioned object is performed by pastilles on the basis of at least partially or completely water soluble, natural and/or synthetic polymers, selected from gums, alginates, carrageens, starch, pectin and gelatin, which are suitable to form gels or viscous solutions in aqueous systems, and further adjuvants and additives, the pastilles containing poly(dimethylsiloxane) (Dimeticon). Surprisingly is has been found that the highly viscous, water insoluble and strongly hydrophobic Dimeticon, can be incorporated in a finely dispersed form into pastilles by an extremely easy way on the basis of the aforementioned natural and/or synthetic polymers.

The term pastilles and particularly the term gum-pastilles according to the present invention comprises those which are prepared by casting. Therefore, the pastilles of the present invention consist of differently shaped elastic formed bodies, containing super finely distributed Dimeticon in a mixture of hydrocolloids and other adjuvants and additives. Gum pastilles are denoted as solid solutions which upon sucking are transformed back to liquid solutions. With the aid of the present invention it is possible to achieve an exact single dosage of the pastille during a relatively careful processing of the ingredients. It is possible to achieve a particularly good incorporation of Dimeticon by using the above mentioned, at least partially or completely water soluble natural and/or synthetic polymers, because processing is possible hereby at relatively low temperatures. Thus a particularly homogeneous distribution of the active substance in the total composition is formed, allowing a dosage of the active substance with a standard deviation in the range from 0,5 to 2%. Furthermore, according to the process of the present invention, it is possible to produce relatively high-concentrated Dimeticon-pastilles.

Especially preferred natural and/or synthetic polymers, according to the present invention, are also known by the term "hydrocolloids". Especially preferred are gums, selected from gum arabic, gelatine and tragacanth. In the same way adjuvants and additives are preferably selected from sugar and/or sugar substitutes, hydrogenated fats, stearic acid, paraffins, oligosaccharides, polysaccharides and/or dextran. Especially preferred saccharides are saccharose and/or glu-cose-syrup.

Corresponding pastilles with other active substances are known per se in the art by the term "gum-pastilles". Their name is derived from the raw material gum arabic incorporated therein. According to the present invention this hydrocolloid is especially preferred as a base material, because it guarantees a slow and uniform melting of the pastille-body upon sucking.

Besides the polymers, the base mass contains particularly flavor carriers like sugar and/or sugar substitutes, because the patient should suck the pastille. Accordingly it is necessary that the pastilles have such a good taste that these are not refused or even swallowed. To improve the taste, as known per se in the art, there are used corresponding adjuvants like saccharose or their substitutes as fructose, hydrogenated glucose-syrup, sorbitol, mannitol and/or xylitol as well as known sweeteners. Besides, there can be used also flavor correcting agents and essences as well as ethereal oils, thereby combining therapeutic effect and improving flavor. Particularly ethereal oils like caraway oil or fennel-oil are suitable to reinforce the antiflatulence effect of Dimeticon.

The disadvantage of chewing tablets among others, is that the tablets are disintegrated by chewing into many tablet pieces of different sizes, or granules which arrive in this form at the stomach, where normally they are not additionally dissolved, so that only a limited part of the active substance will be available.

The pastilles of the present invention are in turn transformed by saliva during chewing into an emulsion or suspension, in which the active substance is present in super finely divided form, and thereby will be completely available for a longer period of time.

The relative amounts of each of the necessary ingredients of the pastilles are less critical. Therefore, the base mass contains, for example, of from 5 to 70% by weight of the polymers based on the total mass of the pastilles. In particular preferred is an amount of from 25 to 60% by weight of gum arabic or from 5 to 20% by weight of gelatin based on the total mass of the pastilles, respectively.

In a further preferred embodiment of the present invention the pastilles contain from 20 to 50% by weight of sugar and/or sugar substitutes based on the total mass of the pastilles.

Commercially available preparations like chewing tablets, capsules or drops, containing the active substance Dimeticon, normally contain from 10 to 200 mg Dimeticon per application doses. Therefore in an particularly preferred embodiment of the present invention there are provided pastilles containing an amount of from 70 to 100 mg of Dimeticon. Normally, the weight of pastille prepared in such a way is about 1 g.

Another embodiment of the present invention consists in a process for the preparation of the pastilles. Hereby in particular the above defined polymers are brought into contact with water and other adjuvants and additives by forming a gel or a viscous solution. Subsequently Dimeticon will be suspended or emulsified into the thus obtained base mass, and afterwards this liquid composition will be cast into forms, dried at room temperature or elevated temperature, in particular from 40° to 70° C., preferably from 50° to 60° C., removed from the form and transferred to a final treatment.

Gum arabic and saccharose are, for example, at the beginning of the preparation process dissolved in water, and Dimeticon is emulsified or suspended into the viscous base mass. This drug mixture will be cast into the so called powder trays and, as described previously, dried, separated from the powder and subjected to a final treatment. The particular advantages of the inventive pastilles and of the process to their preparation are a minor temperature load of the adjuvants and active substances, and their complete homogeneity in the casting mass allowing a high accuracy of the dosage of the active substance. Thereby, the active substance Dimeticon being difficult to handle, is available in a new preparation form.

I claim:

1. Pastilles comprising at least partially water-soluble natural or synthetic polymers selected from the group consisting of gums, alginates, carrageen, pectin and gelatin, wherein the polymers form gels or viscous solutions in aqueous systems, the pastilles containing from 1 to 20% by weight poly(dimethylsiloxane) (Dimeticon).

2. Pastilles according to claim 1, characterized in that the gums are selected from gum arabic, gelatin or tragacanth.

3. Pastilles according to claim 1 or 2, further comprising sugar or sugar substitutes, hydrogenated fats, stearic acid, paraffins, oligosaccharides, polysaccharides or dextran.

4. Pastilles according to claim 3, comprising fructose, sorbitol, mannitol, xylitol, hydrogenated glucose-syrup or sweeteners as sugar substitute.

5. Pastilles according to one of claims 1 or 2, comprising from 5 to 70% by weight of polymers, based on the total mass of the pastilles.

6. Pastilles according to claim 2, comprising from 25 to 60% by weight of gum arabic or from 5 to 20% by weight of gelatin, based on the total mass of the pastilles.

7. Pastilles according to one of claims 1, 2 or 6, comprising from 20 to 50% by weight of sugar or sugar substitutes, based on the total mass of the pastilles.

8. Pastilles according to one of claims 1, 2 or 6, comprising from 7 to 10% by weight, of Dimeticon.

9. Process for the preparation of pastilles, whereby a) at least partially water-soluble natural or synthetic polymers selected from the group consisting of gums, alginates, carrageen, starch, pectin and gelatin, are contacted with water by forming a gel or viscous solution and, Dimeticon is emulsified or suspended into the thus obtained base mass, b) the emulsion according to a) is cast into forms, are and c) is dried at room temperature or elevated temperature to form pastilles.

10. Process according to claim 9, characterized in that the emulsion is dried at a temperature in the range from 40° to 70° C.

11. Process according to claim 9 or 10, characterized in that the dried pastilles are removed from the form.

* * * * *